United States Patent [19]

Schmelz

[11] Patent Number: 5,546,004
[45] Date of Patent: Aug. 13, 1996

[54] SENSOR FOR DETERMINING THE COURSE OF CONCENTRATION OF AN ADSORBENT SUBSTANCE

[75] Inventor: Helmut Schmelz, Prien, Germany

[73] Assignee: Siemens Aktiengesellschaft, Munich, Germany

[21] Appl. No.: 334,860

[22] Filed: Nov. 4, 1994

[30] Foreign Application Priority Data

Nov. 4, 1993 [DE] Germany ............... 43 37 663.0

[51] Int. Cl.⁶ ............... G01N 27/07; G01N 27/26
[52] U.S. Cl. ............... 324/446; 324/439; 324/722; 324/71.1
[58] Field of Search ............... 324/439, 446, 324/450, 722, 71.1; 204/412

[56] References Cited

U.S. PATENT DOCUMENTS

| | | | |
|---|---|---|---|
| 3,714,555 | 1/1973 | Greer | 324/442 |
| 4,553,087 | 11/1985 | Kühn et al. | 324/697 |
| 4,808,931 | 2/1989 | Ling | 324/444 |
| 5,187,096 | 2/1993 | Giaever et al. | 324/439 X |
| 5,353,628 | 10/1994 | Bellows | 324/439 X |
| 5,483,164 | 1/1996 | Moss et al. | 324/425 |

FOREIGN PATENT DOCUMENTS

3305706  4/1985  Germany.
4315278  5/1993  Germany.

*Primary Examiner*—Kenneth A. Wieder
*Assistant Examiner*—Glenn W. Brown
*Attorney, Agent, or Firm*—Herbert L. Lerner; Laurence A. Greenberg

[57] ABSTRACT

A sensor determines a course of concentration of an adsorbent substance, such as ammonia $NH_3$, diffusing out of a flow medium through a surface of a sensor material into the sensor material, as a function of a distance from the surface. Individual pairs of contacts are connected to supply leads and are disposed in the sensor material and optionally on the surface of the sensor material, for determining electrical conductivity of the sensor material between the contacts of the individual pairs of contacts.

16 Claims, 5 Drawing Sheets

SENSOR FOR DETERMINING THE COURSE OF CONCENTRATION OF AN ADSORBENT SUBSTANCE

BACKGROUND OF THE INVENTION

Field of the Invention

The invention relates to a sensor for determining the course of concentration of an adsorbent substance, such as ammonia, that diffuses out of a flow medium through a surface of a sensor material into the sensor material, for determining the course as a function of the distance from the surface.

In the catalytic conversion of at least two reagents of a flow medium, if high degrees of settling are to be attained, it is necessary to put the reagents into contact with a catalyst in a suitable stoichiometric ratio to one another. In the case of the catalytic conversion of nitrogen oxides contained in an exhaust gas or flue gas by the method of selective catalytic reduction (SCR) with ammonia as the reducing agent, for instance, it is necessary for the nitrogen oxides and ammonia to be present at the catalyst in approximately equal portions, averaged over time. Adjusting the requisite stoichiometric ratio of nitrogen oxides to ammonia, or to some substance such as urea that can be converted into ammonia, can be done with satisfaction only if the nitrogen oxide concentration in the exhaust or flue gas can be measured, or can be determined comparatively accurately through a performance graph diagnosis.

However, measuring the nitrogen oxide concentration requires comparatively major effort and entails comparatively great expense. For instance, such measurements can be carried out only in large SCR systems in power plants, but once again a local leakage of ammonia caused by nitrogen oxide skewing can be only unsatisfactorily prevented. Yet avoiding leakage of ammonia must be sought under all circumstances, since ammonia is poisonous and in even extremely slight concentrations ammonia causes annoyance due to human beings to its smell (odor threshold approximately 5 ppm).

Since the nitrogen oxide concentration in fossil-fueled power plant flue gases also only varies slowly when averaged over time, because of load changes that are only slowly completed over time, ammonia metering is carried out with the aid of complicated measurements of nitrogen oxide and optionally of ammonia as well, which measurements have relatively long time constants. Only ammonia metering for flue gases with slowly completed changes in nitrogen oxide concentration can thus be considered to have been achieved somewhat satisfactorily. Removing nitrogen from flue gases emitted by Diesel engines and lean-running engines is significantly more difficult. Due to different operating states and rapid load changes in those engines, a system constructed for those engines with a "controlled Diesel catalyst" (CDC), must be constructed for the resultant major fluctuations in the volumetric flow of exhaust gas, exhaust gas temperature, and nitrogen oxide concentration in the exhaust gas. Since ammonia itself is hazardous and therefore cannot be carried in vehicles, such as passenger cars, trucks, buses, locomotives and ships, the requisite reducing agent is instead carried in the vehicle in the form of an aqueous urea solution, for instance, from which ammonia is then generated, ideally in precisely the quantity needed at the moment.

Since the use of currently known nitrogen oxide sensors in vehicles is extremely improbable because of the major effort and expense involved, the attempt has been made instead to ascertain the quantities of nitrogen oxide produced by the engine per unit of time by a performance graph comparison, adding metered quantities of a suitable reducing agent to those thus calculated quantities of nitrogen oxide, and simulating the settling capacity of the catalyst in an on-board diagnosis system (see German Published, Non-Prosecuted Application DE 43 15 278 A1, for instance). Thus, for the metered addition of the reducing agent in the CDC system, there is thus far no suitable control capability, and as a result if there are defects in the catalyst or at the metering valve, annoyance can be created by excessive leakage of ammonia.

SUMMARY OF THE INVENTION

It is accordingly an object of the invention to provide a sensor for determining the course of concentration of an adsorbent substance, which overcomes the hereinafore-mentioned disadvantages of the heretofore-known devices of this general type and which promotes adjusting the concentration of at least two reagents of a flow medium in a stoichiometric ratio to one another that is advantageous for catalytic conversion of the reagents.

With the foregoing and other objects in view there is provided, in accordance with the invention, in a sensor for determining a course of concentration of an adsorbent substance, such as ammonia $NH_3$, diffusing out of a flow medium through a surface of a sensor material into the sensor material as a function of a distance from the surface, the improvement comprising electric supply leads; and individual pairs of contacts being connected to the supply leads and being disposed in the sensor material and optionally on the surface of the sensor material, for determining electrical conductivity of the sensor material between the contacts of the individual pairs of contacts.

In this way, because of the fact that the specific conductivity of the sensor material depends on the local concentration of the substance adsorbed at the sensor material, a reliable statement can be made as to the course of concentration of the adsorbed substance, as a function of the distance from the surface of the material. Since the adsorbed substance contributes to the catalytic reaction and is consumed in the process, an example being ammonia in the SCR reaction, the electrical resistance measured at the various contact pairs, as a standard for the invoked chemical reduction of the surface in the applicable deep layer of the sensor material, indirectly characterizes the absolute concentration of this substance in the flow medium. This is accomplished because with this sensor it is possible to indicate the quantity that a second reagent, such as nitrogen oxides, penetrating the sensor material from outside and being involved in the catalytic conversion, leaves behind in the various depths of the sensor of the quantities of the first reagent substance that originally penetrated that far and were absorbed there. Especially in the catalytic conversion of nitrogen oxides with ammonia, the thickness of a reaction zone can be determined with the sensor. The thickness of the reaction zone is defined as the depth in the material at which the depth course of the concentration of the ammonia adsorbed at the sensor material passes through a local minimum, which will be described in further detail below in conjunction with the exemplary embodiments.

In accordance with another feature of the invention, in order to determine the depth course, the sensor is constructed in such a way that the pairs of contacts, with the sensor material located between the contacts, are disposed at various distances from the surface in a sensor material layer. In this way, the concentration of a reagent in the sensor material can be measured at various distances from the surface.

In accordance with a further feature of the invention, there is provided a sensor material layer disposed on a substrate layer, in which sensor material layer the pairs of contacts are disposed at various distances from the surface oriented toward the flow medium. In this way, the supply leads to the contact pairs can advantageously be extended through the substrate layer and insulated and supported by means of the substrate layer. Since a columnar disposition of the pairs of contacts is possible in this way, it is also possible for the measured values of electrical conductivity within one line of contact pairs as well as for the depth course of the electrical conductivity optionally to be compared in adjacent columns. As a result, the concentration of the adsorbed substance can be ascertained as a function of a depth region of the sensor. A direct voltage, or a direct voltage having a polarity which is periodically reversed, or an alternating voltage, can be applied successively to the various pairs of contacts, or can also be applied collectively to all of the pairs of contacts simultaneously. The DC or AC resistance or loss angle which is measured in each case can be detected successively chronologically through measurement point reversing switches and analog-to-digital converters.

Precise measurement of the specific conductivity of a depth region requires that the substance adsorbable at the sensor material be allowed to penetrate only through the surface toward the flow medium of the sensor material layer. This is attained, in accordance with an added feature of the invention, if the distances from each contact pair to the surfaces of the sensor material layer not oriented toward the flow medium are greater than the distance of the pair of contacts farthest away from the surface oriented toward the flow medium.

In accordance with an additional, alternative feature of the invention, the surfaces of the sensor material layer that are not oriented toward the flow medium are sealed in gas-tight fashion, which enables the sensor to be made with especially small dimensions. The surfaces not oriented toward the flow medium are those surfaces not exposed to the oncoming flow of the medium.

In accordance with again another feature of the invention, there is provided a substrate layer on which a plurality of the pairs of contacts are disposed and are variously thickly coated with the sensor material.

In accordance with yet another feature of the invention, a first distance between the contacts of one pair of contacts is less than a second distance between immediately adjacently disposed pairs of contacts. This is done for the sake of particularly precise measurement of the specific conductivity of a depth region and therefore for particularly accurate determination of the concentration of the substance adsorbed in this depth region. In this way, voltage incoupling of adjacent contact pairs can largely be suppressed.

In accordance with again a further feature of the invention, the substrate layer contains the electrical supply leads for the sensor material.

In accordance with again an added feature of the invention, there is provided a cylindrical tube having an external thread and surrounding the substrate layer.

In accordance with again an additional feature of the invention, there is provided a layer of the sensor material being applied over the substrate layer, and a cylindrical tube having an external thread and surrounding the substrate layer and the layer of sensor material applied over the substrate layer.

In accordance with still another feature of the invention, the tube is cup-shaped and has a bottom with a polygonal engagement surface for a tool, and the electrical supply leads for the pairs of contacts are extended through the cup bottom.

In accordance with yet a further feature of the invention, there are provided means for temperature stabilization of the sensor material layer and/or for measuring the temperature of the sensor material layer. In this way, corrections in the depth course of the specific conductivity, which are based on a temperature-dependent storage capacity of the sensor material for the adsorbable substance, can largely be eliminated.

In accordance with yet an added feature of the invention, in order to make the sensor especially sensitive to a reducing agent, especially ammonia, urea, or the like, the sensor material includes an oxide having a pH value of less than 7. In oxides with these pH values, the electrical conductivity of the sensor material varies within such limits that it is possible in a simple way, in terms of measuring instruments, to determine the concentration of the adsorbed reducing agent from differences in conductivity.

In accordance with a concomitant feature of the invention, the sensor material includes titanium dioxide $TiO_2$ and one or more of the group of components including tungsten oxide $WO_3$, molybdenum oxide $MOO_3$, vanadium pentoxide $V_2O_5$, and $V_xMo_yO_{32-z}$, where $x+y \leq 12$; $x, y$ are $\geq 1$, and $z \leq 1$.

This sensor material has the same catalytic properties as the catalytically active material used in the catalyst. The depth course of the concentration of the substance adsorbable at the sensor material is therefore directly equivalent to the depth course of the concentration of the substance adsorbed at the catalytically active material. The actual or computational calibration or adaptation of the characteristic of the sensor material for the characteristic of the catalytically active material, which under other circumstances is otherwise necessary, can therefore be omitted. This contributes to an increase in the metering accuracy.

Other features which are considered as characteristic for the invention are set forth in the appended claims.

Although the invention is illustrated and described herein as embodied in a sensor for determining the course of concentration of an adsorbent substance, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

Figure 1:
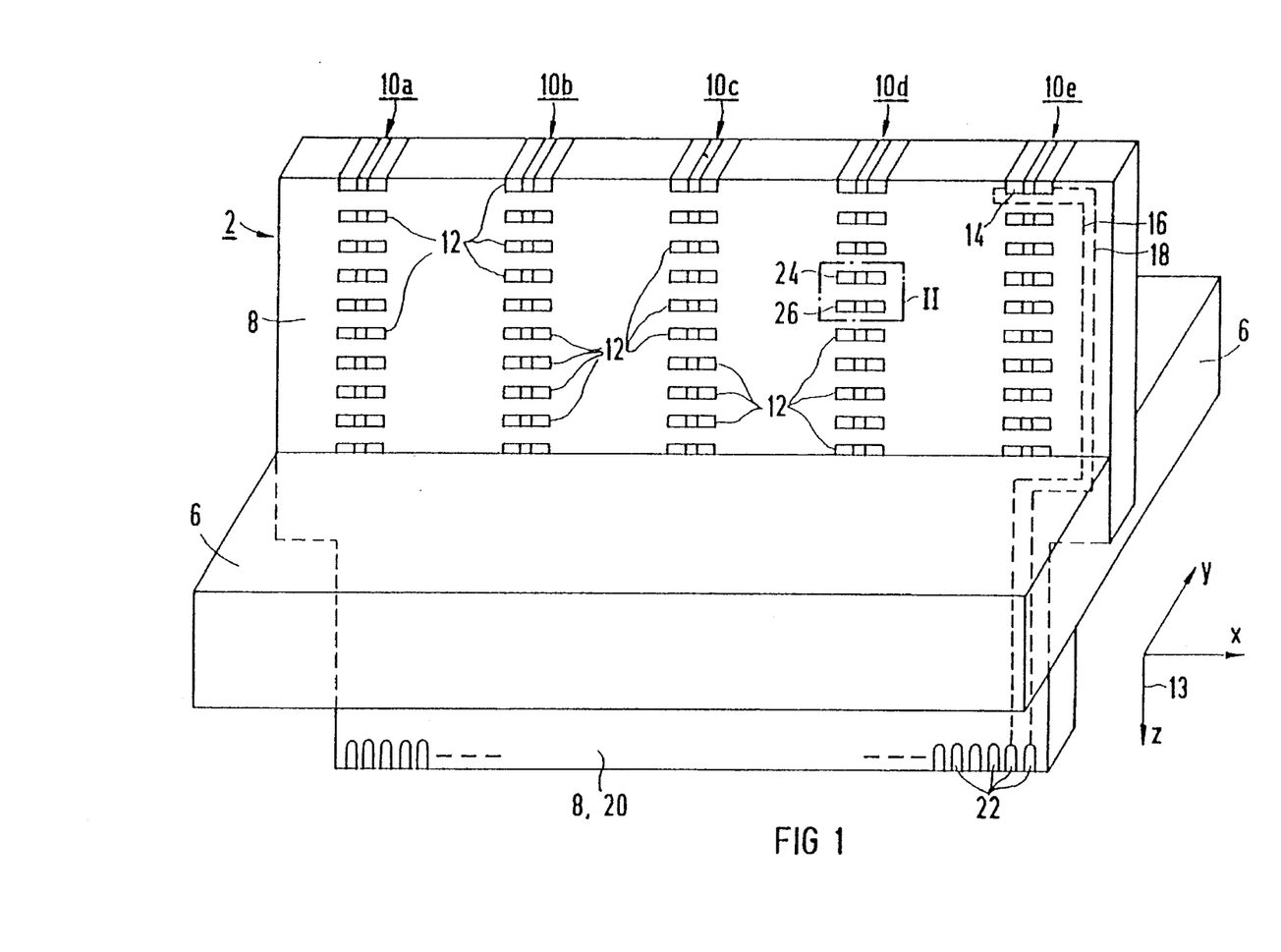
FIG. 1 is a diagrammatic, perspective view of a preliminary stage of a first sensor.
Figure 3:
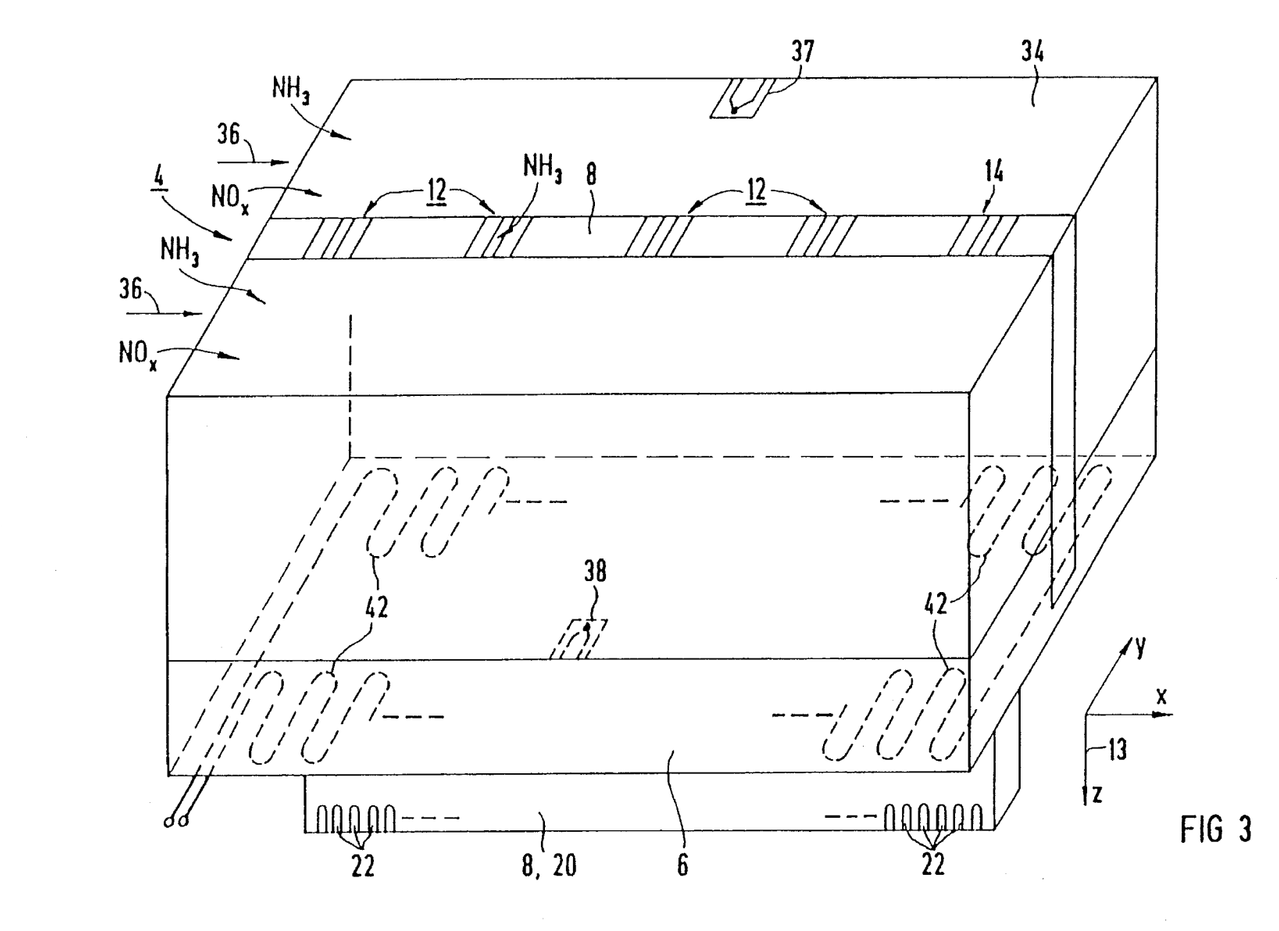
FIG. 3 is a perspective view of a finished first sensor.

DESCRIPTION OF THE PREFERRED EMBODIMENTS:

Referring now to the figures of the drawing in detail and first, particularly, to FIG. 1 thereof, there is seen a preliminary stage 2 of a first sensor 4 seen in FIG. 3, which includes a substrate layer 6 of aluminum oxide $Al_2O_3$, with a layer plane oriented in an xy plane. Inserted into this substrate layer 6 is a further substrate layer that is referred to as a matrix board 8, which is likewise made of aluminum oxide $Al_2O_3$ and is oriented parallel to an xz plane. Five columns 10a–10e each having ten pairs of contacts 12 are disposed in the matrix board 8, above the substrate plane 6. The contact pairs 12 of each column 10a–10d are disposed one above the other and parallel to one another in a z direction. This z direction is equivalent to a penetration direction 13 for an adsorbable material, such as ammonia $NH_3$, that diffuses from a flow medium through a surface 33 of a sensor material 34 into the sensor material 34, as is seen in FIG. 3.

Electric supply leads 16, 18 (represented by dashed lines) are connected at a selected contact pair 14. The electric leads 16, 18 extend inside the matrix board 8, and they end in the form of contact tongues 22, beneath the substrate layer 6, in a piece of the matrix board 8 constructed as a plug 20. The contact tongues 22 are only shown in this case in a portion of the plug 20, but in a finished sensor 4 they extend over the entire width of the plug 20, on both sides of the matrix board 8, in the x direction. The plug 20 can be mounted on a non-illustrated base on which the pairs of contacts 12, 14 can be subjected to a direct voltage, or a periodically reversed-polarity direct voltage, or an alternating voltage, through the electric leads 16, 18. In principle, the plug connection is comparable to a plug connection that is used, for instance, in a personal computer, for connecting graphics cards or cards with digital processors, etc., to a mother board of the personal computer.

The electric leads 16, 18 that are shown in dashed lines in FIG. 1 extend within the matrix board 8 and are insulated from one another and from the outside by the aluminum oxide.

Figure 2:
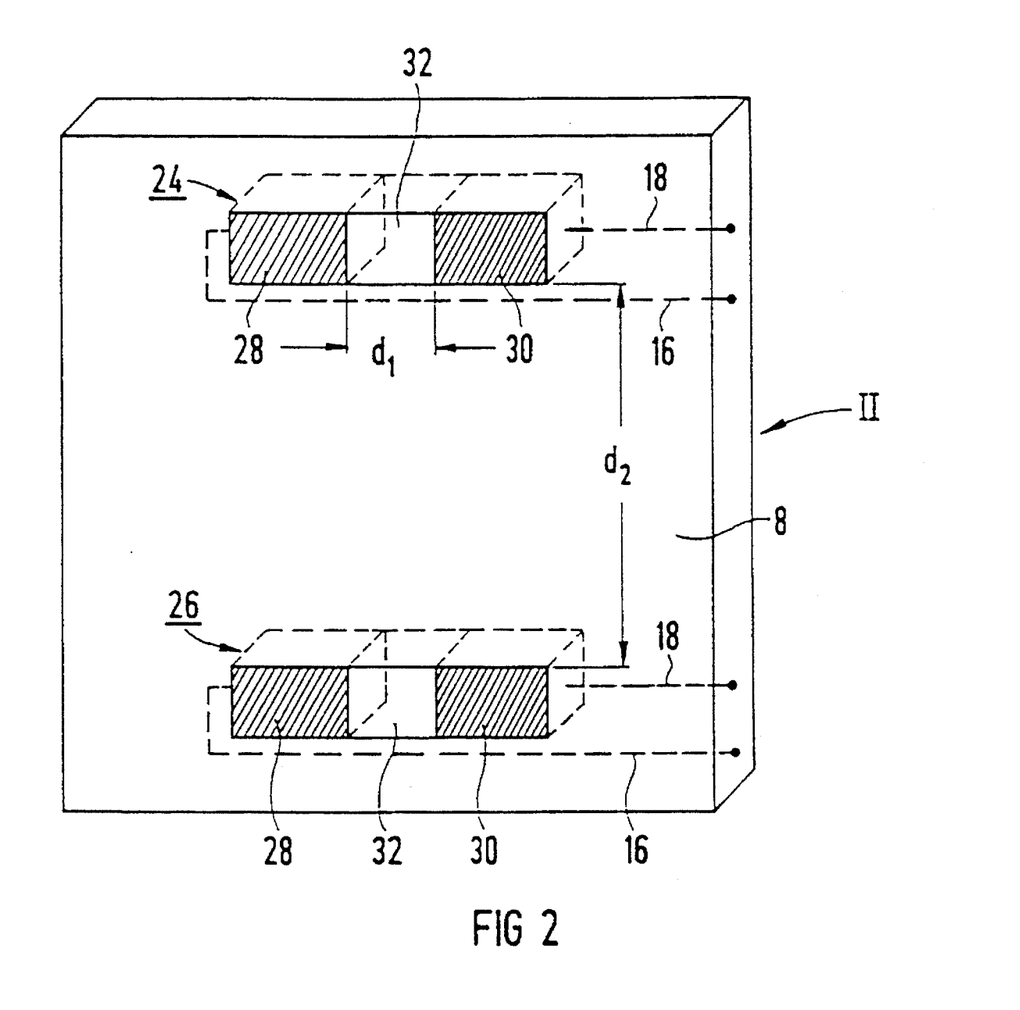
FIG. 2 is an enlarged perspective view of a portion II of FIG. 1.

The portion II of FIG. 1 that is shown in perspective and on a larger scale in FIG. 2, clearly shows a layout of selected pairs of contacts 24, 26, which are identical to the other pairs of contacts 12, 14. Each pair of contacts 24, 26 includes two metal contacts 28, 30, with a passage 32 provided between them for receiving sensor material. Through the use of the contact pairs 24, 26, a voltage that drops across the cube-shaped passage 32 having an edge length $d_1$ of the passage 32 in the sensor material, is measurable through the electric supply leads 16, 18 of these contacts. A distance $d_2$ between two pairs of contacts 24, 26 that are disposed directly one above the other is considerably greater than the distance $d_1$ across which the voltage dropping at the sensor material is measured by means of the contacts 28, 30 for each contact pair 12, 14, 24, 26. It is thus assured that the measured values for the specific conductivity can be ascribed to a defined, three-dimensionally restricted depth region of the sensor material. Distortions in conductivity measurement from incoupling of voltages of other, adjacent contact pairs are largely suppressed in this way.

FIG. 3 shows the finished first sensor 4, with the sensor material layer 34 applied over the substrate layer 6. In the case which is applicable herein of an exhaust gas 36 laden with nitrogen oxides $NO_x$ and ammonia NH3, the sensor material layer 34 includes known $deNO_x$ material, which in the exemplary embodiment includes titanium dioxide and one or more of the following components: tungsten oxide, molybdenum oxide, vanadium pentoxide and $V_xMO_yO_{32-x}$, where x+y $\leq$12; x, y are $\geq$1, and z$\leq$1. Moreover, the finished sensor 4 includes a thermocouple 37 with non-illustrated terminals, on the surface 33 facing toward the exhaust gas 36. A further thermocouple 38 for temperature detection is disposed on a surface opposite the surface 33, or in other words between the substrate layer 6 and the sensor material layer 34. Nickel chromium/nickel thermocouples having thermal voltages which can be picked up at non-illustrated contacts can, for instance, be used as the thermocouples 37, 38. Through the use of the thermocouples 37, 38, it is possible to adjust means 42 for temperature stabilization of the sensor 4, which in this case are present in the form of heating coils 42 (portions of which are shown as dashed lines) that are glued to the lower surface of the substrate layer 6. In the exemplary embodiment, the sensor 4 is temperature-stabilized to approximately 400° C., as a result of which temperature-dependent changes in the adsorption characteristic of the sensor material layer 34 are eliminated. A fixed temperature reference point obtained in this way contributes to making the conductivity values obtained by means of the sensor, and the resultant values for the concentration of the adsorbed ammonia, replicable. The measurement results that are obtained can be adapted to a catalyst which is operated at different temperatures, with knowledge of the absorption characteristic of the sensor material layer 34 as a function of the temperature T.

Figure 4:
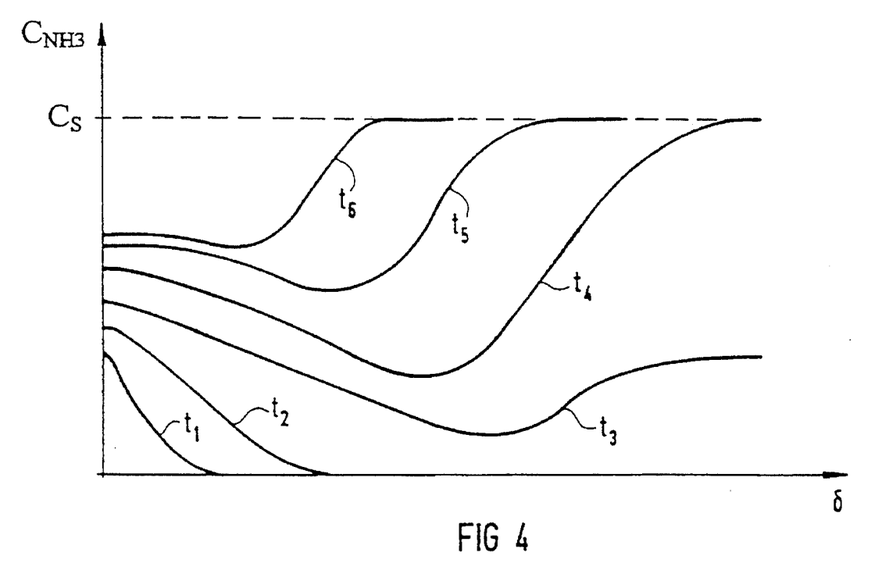
FIG. 4 is a qualitative diagram showing a concentration of ammonia adsorbed at the sensor material as a function of a distance from a surface oriented toward a flow medium, for various times $t_1$ through $t_6$.

FIG. 4 shows courses of concentration of the ammonia adsorbed in the sensor material 34 as measured by means of the sensor 4, as a function of a penetration depth $\delta$ in the sensor material 34, for times $t_1$ through $t_6$. The penetration depth $\delta$ is measured in the positive z direction of FIGS. 1 and 3. On the left side of the diagram, at $\delta=0$, the measured concentration should therefore always be equal to that in the adjacent gas space. The ammonia-free sensor 4 at the time $t_o$ initially only relatively slowly fills with ammonia adsorbed from the exhaust gas 36 (compare the curves for the times $t_1$ and $t_2$). At the time $t_3$, more ammonia is adsorbed in the sensor material 34 than is consumed by the catalytic reduction of nitrogen oxides with ammonia, and as a result there is a local minimum in the concentration of adsorbed ammonia at a penetration depth of approximately 100 μm. As a result of a further metering of ammonia exceeding the concentration of nitrogen oxides in the exhaust gas 36, up to the respective times $t_4$, $t_5$ and $t_6$, the quantities of ammonia adsorbed in the sensor material 34 downstream of a reaction zone (compare the local minimums) increase up to a saturation value $C_s$, which is approximately $10^{19}$ molecules of ammonia per $cm^3$ for the sensor material 34 that is temperature-stabilized to 400° C. An ammonia metering that further remains constant and extends past the time $t_6$ would cause an "over-flow" of the sensor 4. In other words, no further ammonia would be adsorbed in the catalyst, and consequently excess ammonia would leave the catalyst. This would lead to ammonia leakage, which must absolutely be avoided when a CDC is involved. This leakage also rises if the temperature of a catalyst, including the sensor material 34 that is likely filled with ammonia, for instance, rises, particularly at rising exhaust gas temperatures. The specific adsorption capability of the sensor material 34 for ammonia decreases as the temperature rises, and therefore with CDC use the catalyst should never be filled with ammonia up to the capacity limit.

It is possible to determine the nitrogen oxide concentration in the exhaust gas 36 as well as to enable metering of ammonia in a way that is adapted to it, from the course of the thickness of the reaction zone.

Figure 5:
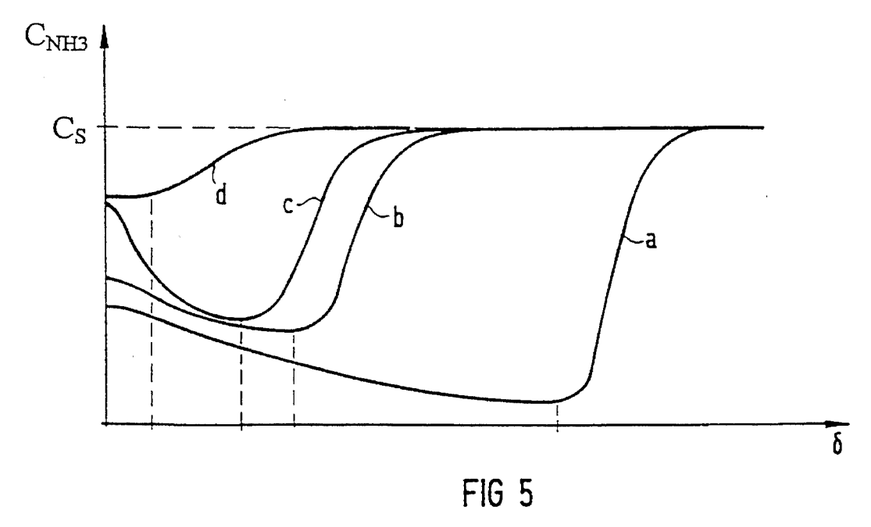
FIG. 5 is a diagram of a qualitative course of the concentration of the ammonia adsorbed at the sensor material, as a function of the distance from the surface oriented toward the flow medium, for various concentrations of ammonia in nitrogen oxide in an exhaust gas.

FIG. 5 shows some typical courses of the concentration of the ammonia adsorbed at a catalyst material, as a function of the penetration depth δ, for various operating states a–d of a Diesel engine. These courses have been determined and interpolated by measuring the course of concentration of ammonia in the sensor 4 that is adsorbed in the sensor material 34.

The operating state a is distinguished by a longer-lasting, the nitrogen oxides $NO_x$ contained in the flue gas 36. By the highly substoichiometric metering of ammonia $NH_3$ relative to time that the nitrogen oxides $NO_x$ have completely finished their reaction, they would have penetrated relatively far into the catalyst material. In this case, the thickness of the reaction zone is only slightly below 200 μm. Since many nitrogen oxide molecules in the upper regions (δ=50 μm) of the catalyst material will not find any reaction partner, a relatively high nitrogen leakage will be obtained in this operating state.

Increasing the metering of ammonia contributes to reducing this leakage, so that with an approximately stoichiometric metering of ammonia, operating states represented by the associated curve courses b and c result. The layer thickness of the reaction zone which is established in these operating states and is between approximately 50 and 80 μm, is advantageous in this exemplary embodiment, as compared with the curve courses a and d and as compared with their operating characteristic. In the operating state d, the concentration of ammonia imported into the exhaust gas 36 predominates over the nitrogen oxide concentration prevailing in the exhaust gas 36. The thickness of the reaction zone recedes relatively strongly, so that within a short time, the adsorption capability of the catalytically active material for ammonia $NH_3$ is exhausted. As a consequence, non-adsorbed ammonia that has also not been consumed in the reduction occurs in the form of leakage. The metering of ammonia should therefore be reduced if this operating state occurs, and as a result the curve course d again approaches the curve courses b, c.

The penetration depths and the thicknesses of the reaction zone shown in FIGS. 4 and 5 are not representative. Instead, they are sensitively dependent on the chemical composition and pore structure of the sensor material 34, on the temperature of the exhaust gas 36 and the sensor material 34, on the flow velocity of the exhaust gas 36, and on the type of oncoming flow (laminar/turbulent). The adsorption characteristic of the sensor material 34 and of the catalytically active material is therefore studied individually as to the dependencies involved. The results of this study are stored in memory, for instance in performance graphs. An on-board diagnosis system in a vehicle can call up these performance graph data and from them derive a metering of the ammonia, for instance in the form of an aqueous urea solution, so that high degrees of settling for the nitrogen oxides contained in the exhaust gas 36 are attainable, with comparatively negligible ammonia leakage.

Figure 6:
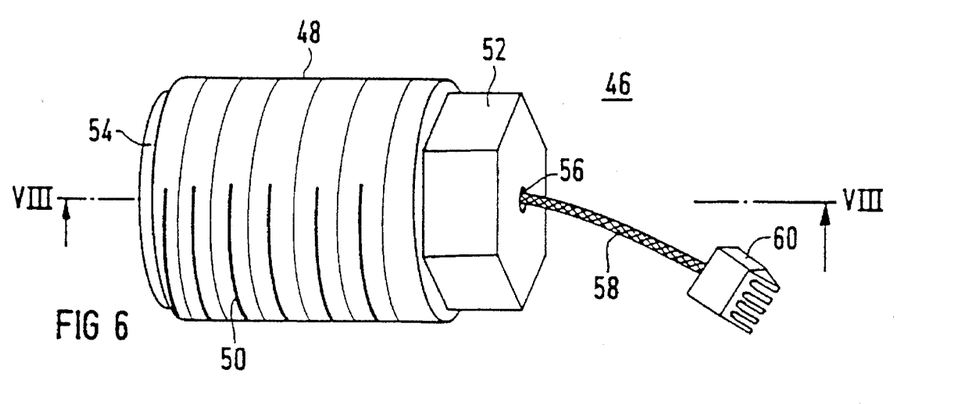
FIG. 6 is a perspective view of a second sensor adapted for use in a vehicle.

FIG. 6 shows a second sensor 46 which is adapted for use in the vehicle and is constructed similarly to a spark plug known from automotive engineering. The sensor 46 includes a cup-like metal body 48, into the outer periphery of which a thread 50 has been cut on a lathe. A cup bottom of the metal body 48 is constructed as a hexagon 52. This hexagon 52 sensor 46 can be screwed into a $deNO_x$ catalyst, for instance, presents an engagement surface to a tool, with which the that has a suitably threaded bore.

Figure 8:
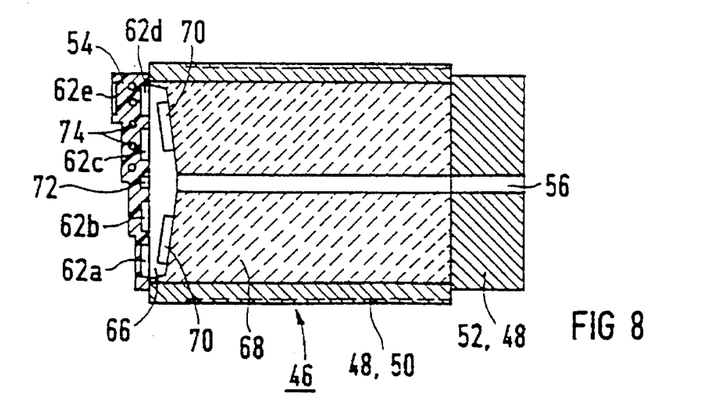
FIG. 8 is a sectional view taken along a line VIII—VIII of FIG. 6, in the direction of the arrows.

As is seen in FIG. 8, an opening in the cup-like metal body 48 is closed by a disk 66 which is set on the metal body 48, which serves as a substrate layer and which has sensor material 54 applied over it with pairs of contacts 62a–62e integrated in the sensor material for conductivity measurement. In addition to the pairs of contacts 62a–62e, a PT100 resistor 72 for temperature measurement as well as small heating coils 70 for temperature stabilization of the sensor material 54 are also integrated with the sensor material 54 in the disk 66, as will be described in further detail below in conjunction with FIG. 8. However, as is seen in FIG. 8, the interior of the cup is filled with a ceramic composition 68 such as aluminum oxide, which has a central bore 56 for electric supply leads 58 of the components which are integrated with the sensor material 54, just like the hexagon 52. In order to carry out resistance measurement, the supply leads 58 are connected through a plug 60 shown in FIG. 6 to a non-illustrated electronic evaluator.

Figure 7:
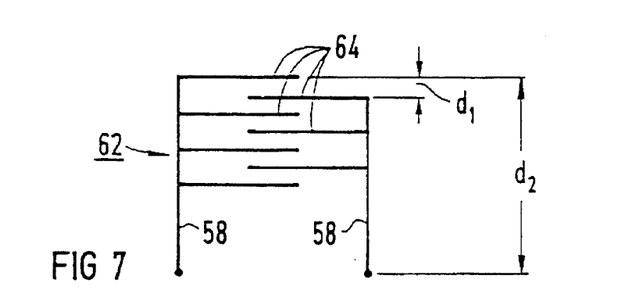
FIG. 7 is a diagrammatic view of one pair of contacts of the sensor of FIG. 6.

FIG. 7 diagrammatically shows one of the pairs of contacts 62a–62e integrated with the sensor material 54. As can be seen from FIG. 7, a distance d1 between two immediately adjacent conductors 64 is considerably smaller than a distance d2 between adjacent pairs of contacts 62. In this way, a resistance dropping integrally across the pair of contacts 62 can be measured without voltage incoupling of adjacent contact pairs 62.

The disposition of the various pairs of contacts 62a–62e can be seen in the sectional view of FIG. 8 which is taken along the line VIII—VIII of FIG. 6 and described below. The contact pairs 62a–62d are applied to the flat disk 66 of aluminum oxide. This disk 66 closes the opening of the cup-like metal body 48.

The heating coils 70 for temperature stabilization of the sensor material 54 are provided beneath the disk 66, on the ceramic aluminum oxide composition 68. No attempt has been made to show the electric supply leads 58 of FIG. 6 for the contact pairs 62a–62e, the heating coils 70 and the PT100 resistor 72 for measuring the temperature of the sensor material 54.

In a departure from the concept on which the sensor 4 of FIGS. 1 and 3 is based, in this case the individual pairs of contacts 62a–62e are variously thickly coated with the sensor material 34 having the composition which is known from FIG. 3, for instance, and which in this case is represented by reference numeral 54 in FIGS. 6 and 8. A reinforcement of glass fibers 74 is moreover provided in the sensor material 54 over the contact pairs 62c and 62d and contributes to improving the adhesion of the sensor material 54 to the aluminum oxide disk 66.

The sensor 46, which is considerably simpler in structure and considerably simpler to produce as compared with the sensor 4 of FIG. 3, naturally operates by the same principle as the sensor 4. Due to the variously high coating thickness, once again in this case as well it is possible to make a statement as to the adsorbed quantity of a substance adsorbed from a flow medium at the sensor material 54 at the particular depth layer. Moreover, in this sensor 46 as well, it can be ascertained by means of the contact pair 62e what quantities of the adsorbed substance, such as ammonia occur at the surface after passing through a certain defined layer thickness, after a pulsed heating of the sensor material 54 by means of the heating devices 70. Thus given suitable following evaluation means, such as an on-board diagnosis system, this sensor 46 likewise assures extensive catalytic conversion of the nitrogen oxides with negligible ammonia leakage.

However, the sensors 4, 46 introduced in this case are also equally suitable for all other catalytic processes in which at least one reagent of a liquid or gaseous flow medium must be present in adsorbed form at the catalyst.

I claim:

1. A sensor for determining a course of concentration of an adsorbent substance diffusing out of a flow medium through a surface of a sensor material into the sensor material as a function of a distance from the surface, the sensor comprising:

a sensor material having an electrical conductivity depending on a local concentration of an adsorbent substance adsorbed at said sensor material;

electric supply leads; and individual pairs of contacts connected to said supply leads and disposed in the sensor material for determining the electrical conductivity of the sensor material between said contacts of said individual pairs of contacts.

2. The sensor according to claim 1, wherein said contacts are disposed on the surface of the sensor material.

3. The sensor according to claim 1, wherein said pairs of contacts are disposed in a layer of the sensor material at various distances from the surface of the sensor material, and the sensor material is disposed between said pairs of contacts.

4. The sensor according to claim 1, including a substrate layer, said sensor material being a layer disposed on said substrate layer in which said pairs of contacts are disposed at various distances from the surface of the sensor material oriented toward the flow medium.

5. The sensor according to claim 4, wherein the sensor material layer has surfaces not being oriented toward the flow medium, one of said pairs of contacts is disposed farthest away from the surface of the sensor material being oriented toward the flow medium, and said contact pairs are disposed at distances from the surfaces of the sensor material layer not being oriented toward the flow medium being greater than the distance of said pair of contacts farthest away from the surface of the sensor material being oriented toward the flow medium.

6. The sensor according to claim 4, wherein said sensor material layer has surfaces not being oriented toward the flow medium but being gas-tightly sealed.

7. The sensor according to claim 4, wherein said substrate layer contains said electrical supply leads for the sensor material.

8. The sensor according to claim 4, including a cylindrical tube having an external thread and surrounding said substrate layer.

9. The sensor according to claim 8, wherein said tube is cup-shaped and has a bottom with a polygonal engagement surface for a tool, and said electrical supply leads for said pairs of contacts are extended through said cup bottom.

10. The sensor according to claim 4, including a layer of the sensor material being applied over said substrate layer, and a cylindrical tube having an external thread and surrounding said substrate layer and said layer of sensor material applied over said substrate layer.

11. The sensor according to claim 1, including a substrate layer on which a plurality of said pairs of contacts are disposed and are variously thickly coated with the sensor material.

12. The sensor according to claim 1, wherein said contacts of one of said pairs of contacts are spaced apart by a first distance, and immediately adjacently disposed pairs of said contacts are spaced apart by a second distance being greater than said first distance.

13. The sensor according to claim 1, including means for stabilizing a temperature of a layer of the sensor material.

14. The sensor according to claim 1, including means for measuring a temperature of a layer of the sensor material.

15. The sensor according to claim 1, wherein the sensor material includes an oxide having a pH value less than 7.

16. The sensor according to claim 1, wherein the sensor material includes titanium dioxide $TiO_2$ and at least one component selected from the group consisting of tungsten oxide $WO_3$, molybdenum oxide $MoO_3$, vanadium pentoxide $V_2O_5$, and $V_xMo_yO_{32-z}$, where $x+y \leq 12$; $x, y$ are $\geq 1$, and $z \leq 1$.

* * * * *